(12) United States Patent
Slemker et al.

(10) Patent No.: US 7,479,163 B2
(45) Date of Patent: Jan. 20, 2009

(54) KNEE DISARTICULATION/LOW-PROFILE PROSTHETIC KNEE-JOINT ASSEMBLY INCLUDING ADJUSTABLE DISTAL COUPLING

(75) Inventors: Tracy C. Slemker, Clayton, OH (US); Steven Steinbarger, Wilmington, OH (US)

(73) Assignee: Prosthetic Design, Inc., Clayton, OH (US)

( * ) Notice: Subject to any disclaimer, the term of this patent is extended or adjusted under 35 U.S.C. 154(b) by 60 days.

(21) Appl. No.: 11/343,192

(22) Filed: Jan. 30, 2006

(65) Prior Publication Data

US 2006/0173554 A1 Aug. 3, 2006

Related U.S. Application Data

(63) Continuation-in-part of application No. 10/251,142, filed on Sep. 20, 2002.

(60) Provisional application No. 60/648,586, filed on Jan. 31, 2005.

(51) Int. Cl.
*A61F 2/80* (2006.01)

(52) U.S. Cl. .................................................... 623/38
(58) Field of Classification Search .............. 623/27–38
See application file for complete search history.

(56) References Cited

U.S. PATENT DOCUMENTS

| 3,659,294 A | 5/1972 | Glabiszewski |
| 4,994,086 A | 2/1991 | Edwards |
| 5,755,813 A | 5/1998 | Krukenberg |
| 5,800,565 A | 9/1998 | Biedermann |
| 5,899,943 A | 5/1999 | Shiraishi et al. |
| 6,033,440 A | 3/2000 | Schall et al. |
| 6,231,618 B1 | 5/2001 | Schall et al. |
| 6,458,163 B1 | 10/2002 | Slemker et al. |

*Primary Examiner*—Bruce E Snow
(74) *Attorney, Agent, or Firm*—Taft Stettinius & Hollister LLP (57) ABSTRACT

Improvements to a prosthetic knee-joint assembly include: a proximal segment having lower-profile design with a surface adapted for mounting to an above-knee prosthetic limb socket; a releasable lock featuring at least one of two complementary surfaces with radial grooves, which increase friction between the two surfaces to prevent rotation or sliding of a coupler component with respect to the knee-joint assembly; and visual indicia markings for determining the position of a distal coupling relative to the distal segment of the knee-joint.

20 Claims, 8 Drawing Sheets

KNEE DISARTICULATION/LOW-PROFILE PROSTHETIC KNEE-JOINT ASSEMBLY INCLUDING ADJUSTABLE DISTAL COUPLING

CROSS-REFERENCE TO RELATED APPLICATIONS

This application is a continuation-in-part of U.S. patent application Ser. No. 10/251,142, filed Sep. 20, 2002, which is published as U.S. Patent Application Publication No. 2004/0059433, the disclosure of which is incorporated herein by reference. This application also claims the priority of U.S. Provisional Patent Application Ser. No. 60/648,586, filed Jan. 31, 2005, the disclosure of which is incorporated herein by reference.

BACKGROUND OF THE INVENTION

The present invention relates generally to prosthetic devices, and more particularly, to a prosthetic knee chassis featuring adjustable couplings provided on or with the proximal and/or distal segments thereof.

Figure 1:
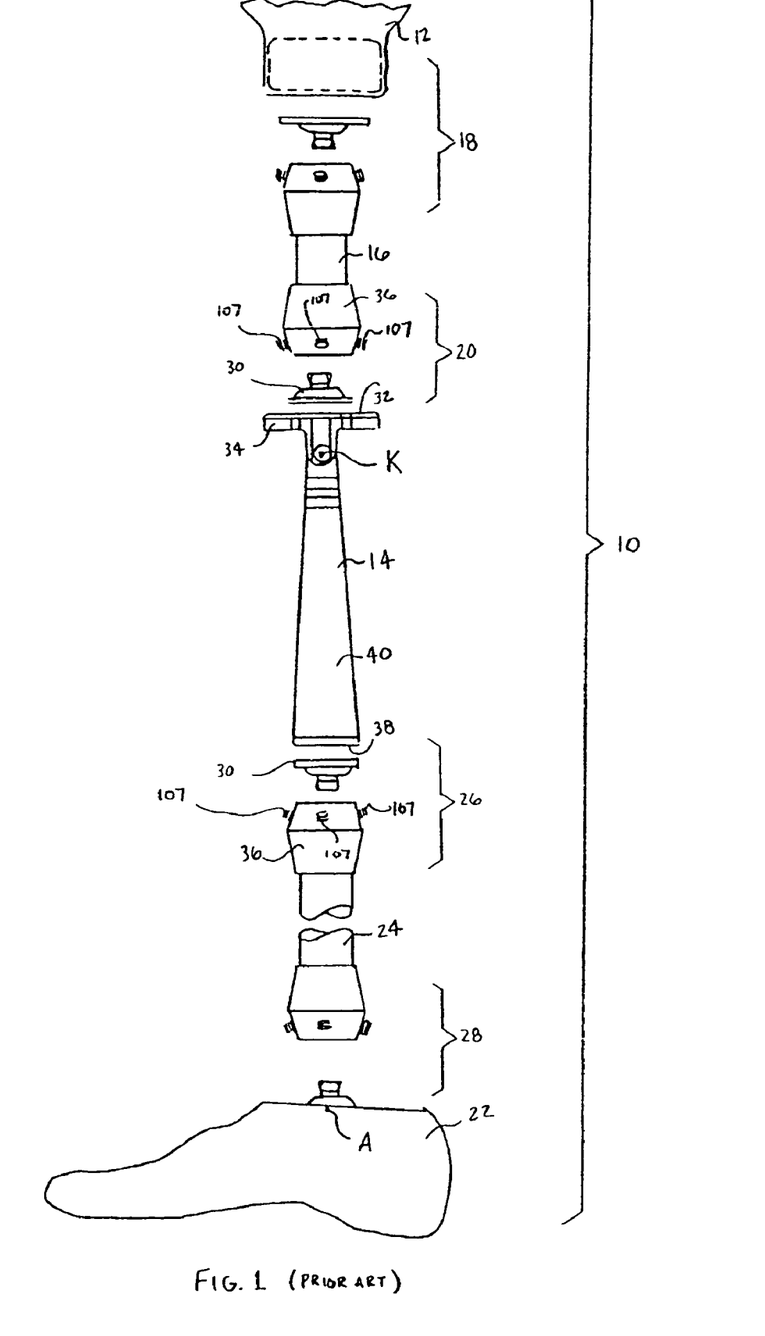
FIG. 1 is a perspective view of an above-knee, prior art prosthetic limb assembly.

As shown in FIG. 1, a conventional prosthetic limb 10 for a transfemoral amputee will include a prosthetic limb socket 12 for receiving the wearer's residual limb, a knee-joint assembly 14, a first pylon component 16 between the prosthetic limb socket 12 and the knee-joint assembly 14, interconnection components 18 for coupling the first pylon 18 to the prosthetic limb socket 12, interconnection components 20 for coupling the first pylon 16 to the knee-joint assembly 14, a prosthetic ankle/foot assembly 22, a second pylon 24 between the knee-joint assembly 14 and the ankle/foot assembly 22, interconnection components 26 for coupling the second pylon 24 to the knee-joint assembly 14 and interconnection components 28 for coupling the second pylon 24 to the ankle-foot assembly 22. The interconnection components 20 may include a conventional pyramid connector 30 mounted to a proximal end 32 of a proximal segment 34 of the knee-joint assembly 14 and a conventional pyramid receiver 36 mounted to a distal end of the first pylon 16. Interconnection components 26 may include a conventional pyramid coupling 30 mounted to a distal end surface 38 of a distal segment 40 of the knee-joint assembly 14 and a conventional pyramid receiver 36 mounted to a proximal end of the second pylon 24. If the prosthetist wishes to provide rotational and/or lateral adjustability with respect to the first pylon 16 and the proximal segment 34 of the knee-joint assembly or wishes to provide rotational and/or lateral adjustability between the distal segment 40 of the knee-joint assembly and the second pylon 24, the prosthetist may wish to replace one or both of the conventional pyramid plates 30 with the adjustable pyramidal link plate assemblies as disclosed in U.S. Pat. Nos. 6,033,440 and 6,231,618. Such adjustable pyramidal link plate assemblies are commercially available from Prosthetic Design, Inc. as component nos. PYR-SL, PYR-SL-R, PYR-TL-SL, PYR-TL-SL-R, Stealth360, and PYR-TL-R.

If a patient has an amputation that occurs at the femoral epicondyles (hereinafter referred to as "knee disarticulation") or has a very long residual limb, then difficulties may arise fitting the aforementioned components of the upright assembly between the distal end of the socket 12 and the floor. Furthermore, the knee center K on the prosthesis 10 may move distally with the addition of components between the distal end of the socket 12 and the knee-joint assembly 14. These components may be of paramount importance when it comes to the static and dynamic alignment of the prosthesis.

The above-mentioned adjustable pyramidal link plate components, in some cases, may add length of the prosthesis so as to offset the knee center of the prosthesis K from the sound side knee center, which may adversely affect the patient's gait pattern. Accordingly, it is desired to provide the adjustability that the prior art adjustable pyramidal link plate assemblies provide (rotational and/or lateral adjustment capabilities) while maintaining a proper knee center with respect to knee disarticulations and long AK amputations.

SUMMARY

The present invention provides a prosthetic knee-joint assembly having adjustable pyramid couplers provided on or with the proximal and/or distal segments of the knee-joint assembly to provide rotational and/or lateral adjustability of the knee-joint assembly with respect to above-knee ("AK") and/or below-knee ("BK") prosthetic limb components without significantly increasing the profile (length) of the knee-joint assembly. Such an invention provides the knee-joint assembly with desired rotational and/or lateral adjustability with respect to AK and/or BK prosthetic limb components while better maintaining a proper knee center with respect to knee disarticulations and long AK amputations.

Accordingly, it is a first aspect of the present invention to provide a prosthetic knee-joint assembly that includes: (a) a proximal segment; (b) a distal segment pivotally disposed with respect to the proximal segment and pivotable with respect to the proximal segment and at least an anterior-posterior direction to provide a knee-joint pivot point; (c) a first coupling provided with the proximal segment, including a first adjustable member having a frustopyramidal boss extending proximally with respect to the proximal segment, where the frustopyramidal boss is adapted to mount the proximal segment to above-knee prosthetic knee components, and where the frustopyramidal boss is slidably adjustable with respect to the proximal segment and rotatably adjustable with respect to the proximal segment; and (d) a second coupling provided with the distal segment, including a second adjustable member having a second frustopyramidal boss extending distally with respect to the distal segment, where the second frustopyramidal boss is adapted to mount the distal segment to below-knee prosthetic limb components, and where the second frustopyramidal boss is slidably adjustable with respect to the distal segment so as to be slidable in at least one of the anterior-posterior and medial-lateral directions, and rotatably adjustable with respect to the distal segment. In a further detailed embodiment, the prosthetic knee-joint assembly further includes: (e) a first releasable lock adapted to selectively prohibit rotation of the first frustopyramidal boss with respect to the proximal segment; (f) a second releaseable lock adapted to selectively prohibit sliding of the first frustopyramidal boss with respect to the proximal segment; (g) a third releaseable lock adapted to selectively prohibit rotation of the second frustopyramidal boss with respect to the distal segment; and (h) a fourth releaseable lock adapted to selectively prohibit sliding of the second frustopyramidal boss with respect to the distal segment.

In a further detailed embodiment, the first and/or second adjustable member is an assembly that includes a sliding member and a rotating member, where the sliding member has a cavity occupied by a lower portion (distal portion for the first adjustable member and proximal portion for the second adjustable member) of the rotating member, where the first cavity includes an annular surface that faces, at least partially, in the downward direction (distal direction for the first adjustable member and proximal direction for the second adjustable member); the rotating member includes a frustopyramidal boss that extends upwardly (proximally in the first adjustable member and distally in the second adjustable member) from the cavity in the sliding member; the lower portion of the rotating member includes an annular surface complimentary to, substantially coaxial with, and facing the annular surface of the cavity; the slidable member includes a pair of opposed surfaces, where each is parallel to the respective direction of slideability, and the opposed surfaces face at least partially in the upper direction (proximal direction with the first adjustable member and distal direction in the second adjustable member); the respective knee segment includes a pair of opposed surfaces complimentary to, substantially parallel to, and facing the opposed surfaces of the adjustable member; and the coupling includes a mechanical press operative to pull the rotating member upwardly (proximal direction with the first adjustable member in distal direction with the second adjustable member) such that the annular surface of the lower portion of the rotating member engages the annular surface of the first cavity in the sliding member, thereby providing the first releaseable lock for the first adjustable member or the third releaseable lock for the second adjustable member; and, thereafter, upon further application of the mechanical press, the combination of the rotating member and the sliding member are pulled in the upward direction (proximal direction with the first adjustable member and distal direction with the second adjustable member) such that the pair of opposed surfaces on the sliding member presses against the complimentary pair of opposed surfaces of the respective knee-joint segment, thereby providing the second releaseable lock with the first adjustable member or the fourth releaseable lock for the second adjustable member.

In yet a further detailed embodiment, the coupling includes a domed member seated on a proximal end of the first segment for the first adjustable member or the distal end of the second segment for the second adjustable member, where the domed member includes a channel extending axially therethrough; the rotating member extends upwardly through the axial channel in the domed member such that the frustopyramidal boss extends above an apex of the domed member and such that the lower portion of the rotating member extends beneath the base of the domed member; and the mechanical press is an annular coupling adapter (also known in the art as a "pyramid receiver") adapted to extend from the above-knee prosthetic limb component or below-knee prosthetic limb component, where the mechanical press includes at least two of the diametrically opposed set screws extending radially into the central channel of the pyramid receiver.

It is a second aspect of the present invention to provide a prosthetic knee-joint assembly for a prosthetic limb that includes: (a) a proximal segment; (b) a distal segment pivotally disposed with respect to the proximal segment and pivotable with respect to the proximal segment in at least an anterior-posterior direction to provide a knee-joint pivot point; and (c) a male coupling provided with at least one of the proximal segment and the distal segment, where the male coupling includes a frustopyramidal boss extending outwardly from the one segment substantially approximate the TKA line, the frustopyramidal boss being adapted to mount the one segment to a female coupling carried on another prosthetic limb component, and the frustopyramidal boss being slidably adjustable with respect to the one segment so as to be slidable in at least one direction substantially perpendicular to the TKA line, and the frustopyramidal boss being rotationally adjustable with respect to the one segment so as to be rotatable with respect to the one segment on a rotational axis substantially parallel to the TKA line. In a more detailed embodiment, the male coupling is an assembly that includes a sliding member slidably carried by the one segment and a rotating member rotatably carried by the sliding member, and the rotating member has a first end carried by the sliding member and an opposite end that includes the frustopyramidal boss. In yet a further detailed embodiment, the one segment includes a dove-tail shaped channel in an end surface thereof, the sliding member includes at least a portion that has a dog-tail shaped cross-section complimentary to the dove-tail shaped channel in the one segment, where the portion is slidably carrier in the dove-tail shaped channel; and the sliding member includes an annular cavity extending into an end surface thereof, where the annular cavity retains the first end of the rotating member therein.

It is a third aspect of the present invention to provide a prosthetic knee-joint assembly for a prosthetic limb that comprises: (a) a proximal segment including a planar proximal surface and a first groove extending into and along the proximal surface; (b) a distal segment pivotally disposed with respect to the proximal segment, and pivotable with respect to the proximal segment in at least the anterior-posterior direction to provide a knee-joint pivot point, the distal segment including a planar distal surface and a second groove extending into and along the distal surface; (c) a first coupling including a first bearing portion slidably received within the first groove and further including a first frustopyramidal boss extending in a proximal direction from the first bearing portion, where the first frustopyramidal boss is rotatable with respect to the first bearing portion and adapted to mount the proximal segment to AK prosthetic limb components; (d) a second coupling including a second bearing portion slidably received within the second groove and further including a second frustopyramidal boss extending in a distal direction from the second bearing portion, where the second frustopyramidal boss is rotatable with respect to the second bearing portion and adapted to mount the distal segment to BK prosthetic limb components; (e) a first releaseable lock adapted to selectively prohibit rotation of the first frustopyramidal boss with respect to the first bearing portion; (f) a second releaseable lock adapted to selectively prohibit sliding of the first bearing portion in the first groove; (g) a third releaseable lock adapted to selectively prohibit rotation of the second frustopyramidal boss with respect to the second bearing portion; and (h) a fourth releaseable lock adapted to selectively prohibit sliding of the second bearing portion in the second groove. In a more detailed embodiment, the first coupling includes a first domed portion positioned proximally to the proximal surface of the proximal segment and proximally to the first bearing portion; the first frustopyramidal boss extends from the first bearing portion, axially through the first domed portion, and out from a proximal apex of the first domed portion; the second coupling includes a second domed portion positioned distally to the distal surface of the distal segment and to the second bearing portion; and the second frustopyramidal boss extends from the second bearing portion, axially through the second domed portion, and out from a distal apex of the second domed portion.

It is a fourth aspect of the present invention to provide a prosthetic knee-joint for a prosthetic limb that includes: (a) a proximal segment; (b) a distal segment pivotally disposed with respect to the proximal segment and pivotable with respect to the proximal segment in at least an anterior-posterior direction to provide a knee-joint pivot point; (c) a first coupling at least partially received within a first groove, depression or cavity extending into a proximal end of the proximal segment, where the first coupling is adapted to mate with and couple to an above-knee prosthetic limb component, and where the first coupling includes a first frustopyramidal boss that is slidably adjustable with respect to the proximal segment and rotationally adjustable with respect to the proximal segment; and (d) a second coupling at least partially received within a second groove, depression or cavity extending into a proximal end of the distal segment, where the second coupling is adapted to mate with and couple to a below-knee prosthetic knee component, and where the second coupling includes a second frustopyramidal boss, that is slidably adjustable with respect to the distal segment and rotationally adjustable with respect to the distal segment.

It is a fifth aspect of the present invention to provide a prosthetic knee-joint assembly for a prosthetic limb that includes: (a) a proximal segment; (b) a distal segment pivotably disposed with respect to the proximal segment and pivotable with respect to the proximal segment in at least an anterior-posterior direction to provide a knee-joint pivot point; (c) a first coupling at least partially received with a first groove extending into a proximal end of the proximal segment, including a first adjustable member having a frustopyramidal boss extending proximally with respect to the proximal segment, where the first frustopyramidal boss is adapted to mount the proximal segment to above-knee prosthetic limb components, and where the first adjustable member is slidably mounted to the proximal segment so as to be slidable in either the anterior-posterior or medial-lateral directions; and (d) a second coupling at least partially received within a second groove extending into the distal segment, including a second adjustable member having a second frustopyramidal boss extending distally with respect to the distal segment, where the second frustopyramidal boss is adapted to mount the distal segment to below-knee prosthetic limb components, and where the second adjustable member is slidably mounted to the distal segment so as to be slidable in the opposite direction as compared to the first coupling.

In a detailed embodiment of this fifth aspect of the present invention, the prosthetic knee-joint assembly further includes: (e) a first releaseable lock adapted to selectively prohibit sliding of the first adjustable member with respect to the proximal segment; and (f) a second releaseable lock adapted to selectively prohibit sliding of the second adjustable member with respect to the distal segment. In yet a further detailed embodiment, the first adjustable member includes a pair of opposed surfaces, each being parallel to the respective direction of slidability and facing at least partially in a proximal direction; the first groove includes a pair of opposed surfaces complimentary to, and substantially parallel to, and facing the pair of opposed surfaces of the first adjustable member; and the first coupling includes a mechanical press operative to pull to first adjustable member in the proximal direction such that the pair of opposed surfaces of the first adjustable member presses against the complimentary pair of opposed surfaces of the proximal segment, thereby providing the first releaseable lock. In yet a further detailed embodiment, the first coupling includes a domed member seated on a proximal end of the first segment and having a channel extending axially therethrough; the first adjustable member extends through the axial channel in the domed member such that the first frustopyramidal boss extends out from an apex of the domed member in such that the pair of opposed surfaces of the first adjustable member extend out from the base of the domed member; and the mechanical press is an annular coupling adapter (pyramid receiver) extending from the above-knee prosthetic limb component whereupon tightening of the set screws in the annular coupling adapter causes the set screws to contact and press against opposed surfaces of the first frustopyramidal boss such that the first adjustable member is pushed by the set screws in the proximal direction. In yet a further detailed embodiment, the frustopyramidal boss is also rotatably adjustable with respect to the proximal segment so as to be rotatable with respect to the proximal segment.

It is a sixth aspect of the present invention to provide a knee-joint assembly for a prosthetic limb that includes: (a) a proximal segment; (b) a distal segment pivotably disposed with respect to the proximal segment and pivotal with respect to the proximal segment in at least an anterior-posterior direction to provide a knee-joint pivot point; and (c) a coupling provided on one or both of the proximal segment and the distal segment, where the coupling includes an adjustable member having a frustopyramidal boss extending outwardly from the respective segment substantially along the TKA line, where the frustopyramidal boss is adapted to mount the respective segment to another prosthetic limb component, and where the adjustable member is slidably mounted to the respective segment so as to be slidable in a direction perpendicular to the TKA line. In a more detailed embodiment, the respective segment includes a channel extending in the respective direction of slidability, where the channel includes a pair of opposed surfaces parallel to the respective direction of slidability; the adjustable member includes a portion carried in the channel of the respective segment, where the carried portion of the adjustable member includes a pair of opposed surfaces complimentary to, substantially parallel to, and facing the pair of opposed surfaces of the channel in the respective segment; and the coupling includes a mechanical press operative to press the pair of opposed surfaces of the carried portion against the complimentary pair of opposed surfaces in the channel of the respective segment, thereby selectively inhibiting sliding of the adjustable member with respect to the respective segment.

It is a seventh aspect of the present invention to provide a prosthetic knee-joint assembly that includes: (a) a proximal segment; (b) a distal segment pivotally disposed with respect to the proximal segment and pivotable with respect to the proximal segment in at least an anterior-posterior direction to provide a knee-joint pivot point; (c) a first coupling at least partially received within a proximal end of the proximal segment, adapted to mate with and couple to an above-knee prosthetic limb component, where the first coupling is selectively slidable with respect to the proximal segment in at least a first direction substantially perpendicular to the TKA line; and, optionally, (d) a second coupling at least partially received within a distal end of the distal segment, adapted to mate with and couple to a below-knee prosthetic limb component, where the second coupling is selectively slidable with respect to the distal segment in at least a second direction substantially perpendicular to the TKA line. In a more detailed embodiment, the knee-joint assembly further includes: (e) a first releaseable lock for selectively prohibiting sliding of the first coupling with respect to the proximal segment; and (f) a second releaseable lock for selectively prohibiting sliding of the second coupling with respect to the distal segment. In yet a further detailed embodiment, the first and second releaseable locks are adapted to be accessible, lockable and un-lockable without having to completely de-couple their respective first and second couplings from the corresponding above-knee and below-knee prosthetic limb components.

It is an eighth aspect of the present invention to provide a prosthetic knee-joint assembly for a prosthetic limb that includes: (a) a proximal segment; (b) a distal segment pivotally disposed with respect to the proximal segment, and pivotable with respect to the proximal segment in at least an anterior-posterior direction to provide a knee-joint pivot point; (c) a first coupling at least partially received within a proximal end of the proximal segment, adapted to mate with and couple to an above-knee prosthetic limb component, where the first coupling is selectively rotatable with respect to the proximal segment; and, optionally, (d) a second coupling at least partially received within a distal end of the distal segment, adapted to mate with and couple to a below-knee prosthetic limb component, where the second coupling is selectively rotatable with respect to the distal segment. In a more detailed embodiment, the knee-joint assembly further includes: (e) a first releaseable lock for selectively prohibiting rotation of the first coupling with respect to the proximal segment; and (f) a second releaseable lock for selectively prohibiting rotation of the second coupling with respect to the distal segment. In yet a further detailed embodiment, the first and second releaseable locks are adapted to be accessible, lockable and un-lockable without having to completely de-couple the respective first and second couplings from the corresponding above-knee and below-knee prosthetic limb components.

It is a ninth aspect of the present invention to provide a prosthetic knee-joint assembly for a prosthetic limb that includes: (a) a proximal segment; (b) a distal segment pivotally disposed with respect to the proximal segment, and pivotable with respect to the proximal segment in at least an anterior-posterior direction to provide a knee-joint pivot point; and (c) an adjustable coupling at least partially received within and/or integrated within an end of either the proximal segment or the distal segment, where the coupling is adapted to mate with and couple to a respective above-knee or below-knee prosthetic limb component, and where the coupling is selectively rotatable and/or slidable with respect to the respective knee-joint segment.

It is a tenth aspect of the present invention to provide a prosthetic knee-joint assembly for a prosthetic limb that features: a proximal segment having lower-profile design with a surface adapted for mounting to an above-knee prosthetic limb socket; a releasable lock featuring at least one of two complementary surfaces with radial grooves, which increase friction between the two surfaces to prevent rotation or sliding of a coupler component with respect to the knee-joint assembly; and visual indicia markings for determining the position of a distal coupling relative to the distal segment of the knee-joint, in addition to the features and embodiments described above with respect to the first through ninth aspects.

These and other aspects and embodiments will be apparent from the following description, the accompanying drawings, and the appended claims.

DETAILED DESCRIPTION

Figure 2:
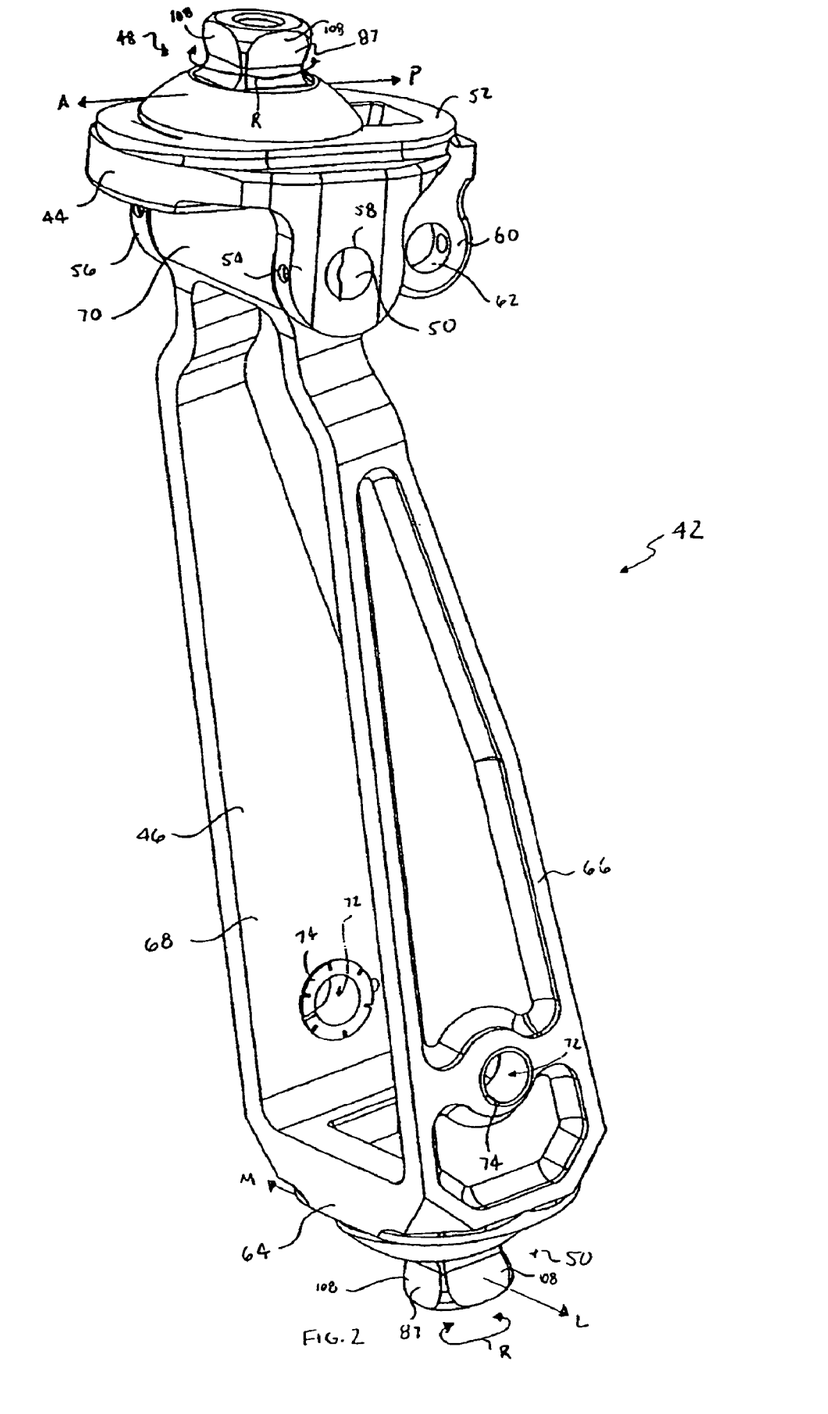
FIG. 2 is a perspective view of a knee joint assembly for a prosthetic limb according to a first exemplary embodiment of the present invention.
Figure 3:
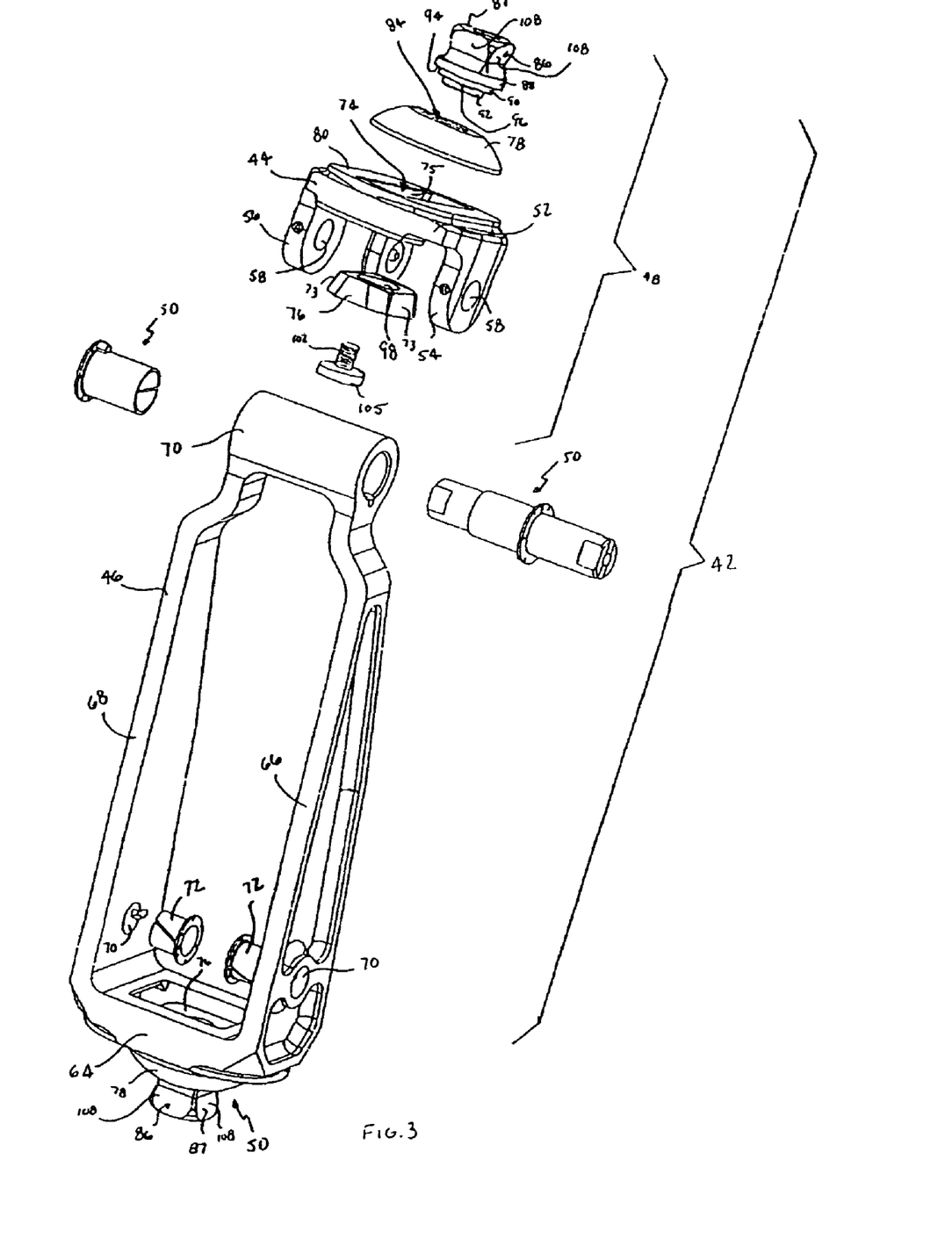
FIG. 3 is a perspective, exploded view of the knee-joint assembly of FIG. 2.
Figure 4:
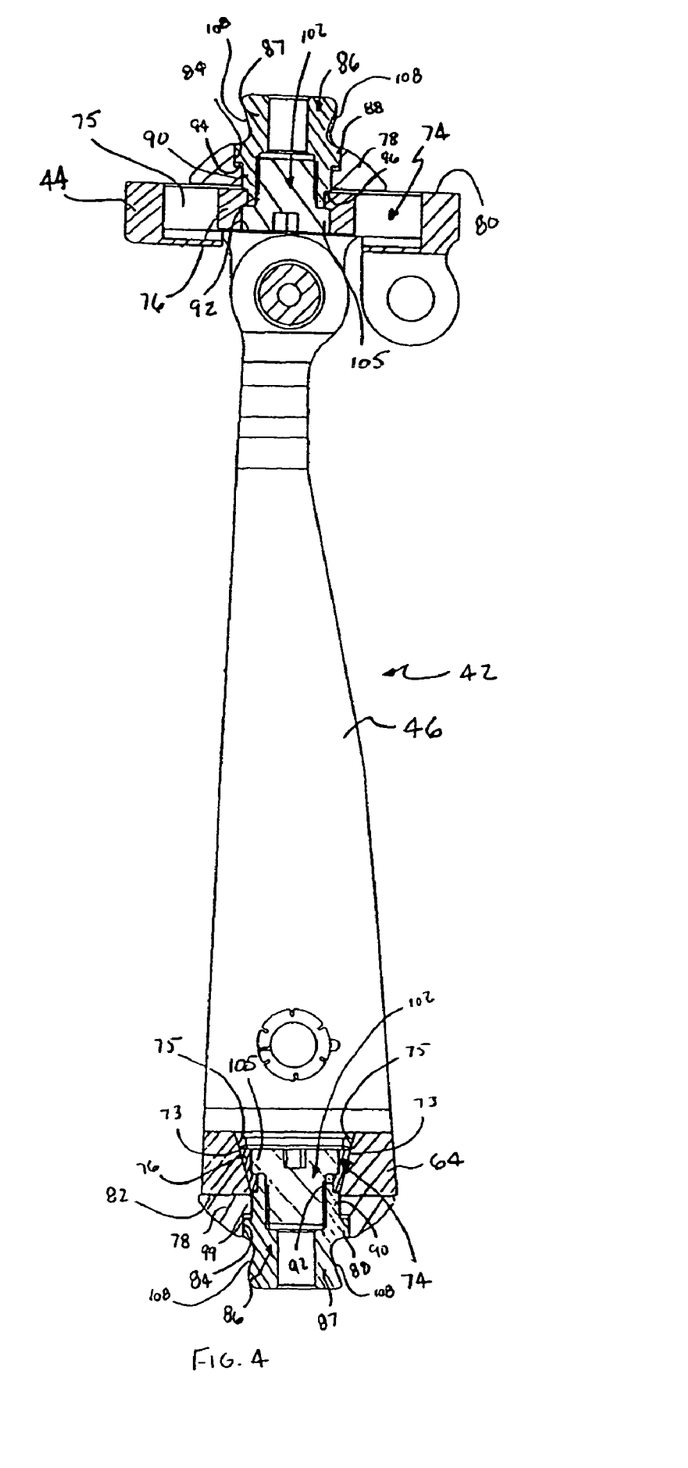
FIG. 4 is a cross-sectional, side elevational view of the knee-joint assembly of FIGS. 2 and 3.

As shown in FIGS. 2-4, a first exemplary embodiment of the present invention is a prosthetic knee-joint assembly or knee-chassis 42, having adjustable coupling components provided with its proximal and distal segments 44, 46. In the present exemplary embodiment, the adjustable coupling on the proximal segment 44 is a male pyramid component assembly 48 that is slidably adjustable in the anterior-posterior direction and that is also rotationally adjustable. The coupling component provided on the distal segment 46 is an adjustable pyramid assembly 50 that is slidingly adjustable in the medial-lateral directions and is also rotationally adjustable. The proximal segment 44 is pivotally coupled to the distal segment 46 by a nylon hinge assembly 50 such that the proximal segment 44 will be pivotable with respect to the distal segment 46 in the anterior-posterior direction. Generally the proximal segment 44 includes a substantially planar base 52 at a proximal end thereof and includes a pair of axially extending arms 54, 56 extending from the medial and lateral sides of the planar base, where each of the arms 54, 56 include holes extending therethrough for receiving the hinge assembly 50. The proximal segment 44 also includes a posterior projection 60 extending distally therefrom which includes a hole 62 extending therethrough to which is adapted to be coupled to a hydraulic or pneumatic piston assembly for the prosthetic knee (not shown). The distal segment 46 generally includes a substantially planar base 64 at a distal end thereof and a pair of proximally extending legs 66, 68 extending from the medial and lateral sides of the base 64 to a proximal end where the legs 66, 68 meet at a hollow cylinder extending perpendicularly therefrom in the medial-lateral direction, into which is received the hinge assembly 50. Each of the legs 66, 68 include a hole 72 extending therethrough approximate a distal end of the respective leg, where each hole receives a nylon bushing 74. As will be apparent to those of ordinary skill such holes 72 provide a distal coupling for the hydraulic or pneumatic piston assembly of the prosthetic knee.

In the exemplary embodiment, each of the adjustable coupling assemblies 48, 50 are constructed in substantially similar fashions using substantially similar components. The primary difference between the two couplings, in the exemplary embodiment, is that the proximal coupling 48 is slidably adjustable in the anterior-posterior directions while the distal coupling is slidably adjustable in the medial-lateral directions. For the sake of clarity, the construction of the coupling assemblies will be discussed using identical numerals and orientational reference directions. For example, with the following disclosure, the "up" direction is the proximal direction for the proximal coupling assembly 48 and is the distal direction for the distal coupling assembly 50. Likewise, the "down" direction is the distal direction for the proximal coupling assembly 48 and the proximal direction for the distal coupling assembly 50. Any other substantial differences between the proximal and distal coupling assemblies 48, 50 will be noted when necessary.

Figure 5:
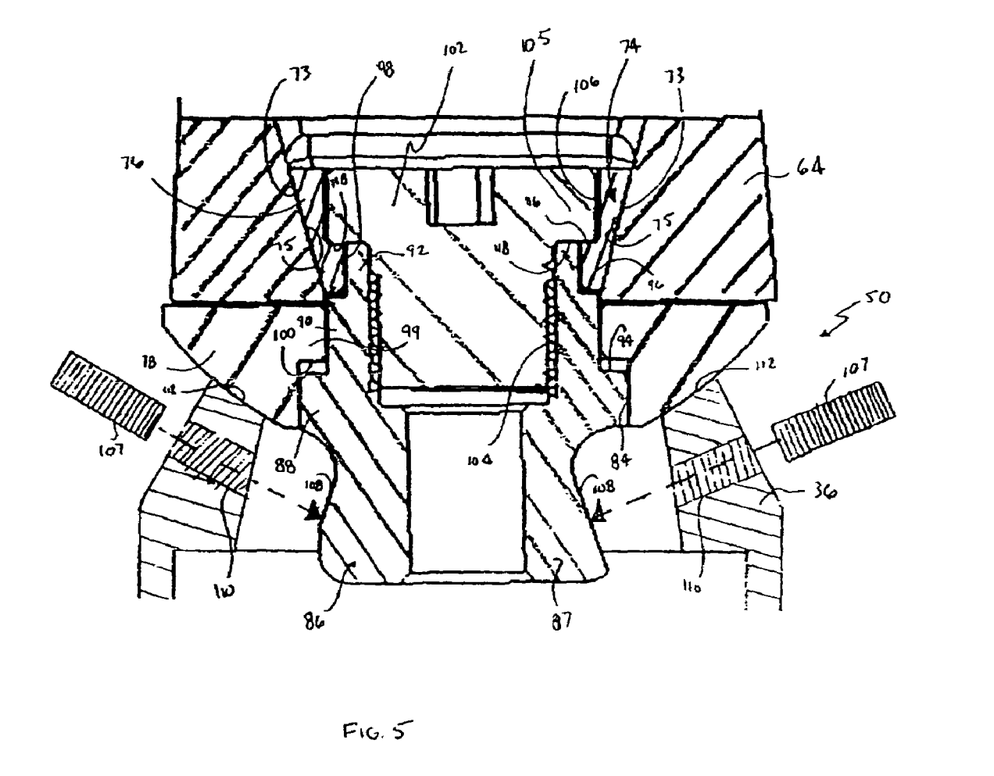
FIG. 5 is a magnified view of the portion of FIG. 4 within the circle 5.

As shown specifically in FIGS. 3 through 5, the planar base portion 52 of the proximal segment and the planar base portion 64 of the distal segment 46 each include a dovetail shaped (in cross-section) channel or groove 74 extending axially therethrough. The dove-tail shaped groove 74 in the proximal member 44 extends along the planar base 56 in the anterior-posterior directions while the dove-tail shaped groove in the distal member 46 extends along the planar base 64 in the medial-lateral directions. Each of the adjustable coupling assemblies 48, 50 include a dove-tail shaped (in cross-section) base component 76 carried within the dove-tail shaped groove 74. The dove-tail shaped base component 76 is oriented within the dove-tail shaped groove 74 such that the upwardly and outwardly facing angled surfaces 73 of the dovetail shaped base component 76 face the downwardly and inwardly facing angled surfaces 75 of the dove-tail shaped groove 74.

A flat-topped dome member 78 resides on each of the flat proximal surface 80 of the planar base 44 and the flat distal surface 82 of the distal base 64. Each dome 78 includes an axial channel 84 extending therethrough for receiving a pyramidal boss component 86 therein. The dome also includes an annular projection 99 extending radially into the axial channel 84. The upper end of the pyramidal boss component 76 includes a frustopyramidal boss 87 of conventional design and the lower end of the pyramidal boss 86 includes three cylindrical, coaxial segments 88, 90, 92, the diameters of which decrease towards the lower end of the pyramidal boss component 86 to provide two, downwardly facing, annular shoulders: a first annular shoulder 94 on the first cylindrical segment 88 and a second annular shoulder 96 on the second cylindrical segment 90. The portion of the cavity 84 above the annular projection 99 has a diameter slightly greater than the diameter of the cylindrical segment 88 of the pyramidal boss 86 component and the inner diameter of the radial projection 99 is slightly larger than the outer diameter of the cylindrical segment 90 of the pyramidal boss competent such that when the pyramidal boss component is received within the axial channel 84 of the dome member 78 the frustopyramidal boss 87 will extend from the apex of the dome and the shoulder 100 of the dome member 78 will abut the shoulder 94 of the pyramidal boss 86, thereby preventing the boss 87 from falling below the dome member.

The lower-most cylindrical segment 92 of the pyramidal boss 86 extends into the axial channel 98 of the dove-tail shaped member 76 where the outer diameter of the lower most segment 92 is slightly less than the inner diameter of the axial channel 98. A threaded bolt 102 extends upwardly into the bottom of the axial channel 98 and mates with a threaded bore 104 extending into the bottom of the pyramidal boss component 86. The lower end of the bolt 102 includes a flange 105 that is seated within a counter-bore 106 of the dove-tail shaped member 76. Therefore, when the bolt 102 is threaded into the threaded bore 104 of the pyramidal boss component 86 (preferably using a LOCTITE.RTM. thread-locking solution) the bolt 102 and pyramidal boss component 86 assembly essentially become a unitary component that freely carries the dome 78, respective knee-chassis segment (44 or 46) and dove-tail shaped boss component 76 there-between such that the couplings (48 and 50) are essentially integrated with their respective knee-chassis segments (44 or 46).

The various components of the couplings (48 and 50) have a certain amount of axial play built in such that the pyramidal boss component 86 is able to be rotated with respect to the dove-tail shaped base component 76 and, in turn, the respective knee-chassis segment (44 or 46). Likewise, the built in axial play between the components allows the dove-tail shaped base component 76 to be slid within the dove-tail shaped groove 74 and, in turn, the entire coupling (48 and 50) is slidable with respect to the respective knee-chassis segment (44 or 46). Referring to FIG. 2, the proximal coupling 48 is slidable in the anterior-posterior directions as shown by arrows A-P and the frustopyramidal boss 87 is rotatable with respect to the coupling 48 in the direction as shown by arrow R. Likewise, the coupling 50 on the distal knee-chassis segment 46 is slidable in the medial-lateral directions as shown by arrows M-L and the frustopyramidal boss 87 is rotatable with respect to the rest of the coupling 50 in the direction shown by arrow R.

Referring specifically to FIG. 5, in the exemplary embodiment, when the couplings 48, 50 are mated with their respective pyramid receiving components 36 the tightening of the set screws 107 of the pyramid receiver components against the inwardly angled side faces 108 of the frustopyramidal boss 87 essentially provides a mechanical press that locks the component, restricting any further rotational and/or sliding adjustments of the component with respect to the respective knee-chassis segment. This threaded mechanical press operates as follows: initially, when the set screws 107 are threaded through the correspondingly threaded holes 110 in the pyramid receiver 36 (which are angled radially inwardly and upwardly) against the angled surfaces 108 of the frustopyramidal boss 87, causing the pyramidal boss component 86 to be pushed in the upward direction, while simultaneously causing the domed member 78 to be pushed by the lower end 112 of the pyramid receiver 36 in the downward direction such that the domed member 78 abuts the upper surface of the respective planar base 52, 64; as the pyramidal boss component 86 is pulled in the upper direction with respect to the respective planar segment 52, 64, the flange 105 of the attached bolt 102 contacts the upper shoulder 116 of the counter-bore 106 in the dove-tail shaped base component 76, which, in turn, pulls the dovetail shaped base component upwardly such that the upwardly and outwardly facing angled surfaces 73 of the dove-tail shaped base component 76 press against the downwardly and inwardly facing angled surfaces 75 of the dove-tail shaped groove 74 (effectively locking the dove-tail shaped base component 76 from sliding within the dove-tail shaped groove 74, and, in turn, locking the respective coupling component 48, 50 from sliding with respect to the respective knee-chassis segment 44, 46); and, further, such tightening of the set screws 107 and subsequent pushing of the pyramidal boss component 86 causes the upper surface 118 of the radial flange 105 of the bolt component 102 to press against the downward facing annular shoulder surface 116 in the counter-bore 106 of the dove-tail shaped base component 76 effectively prohibiting the pyramidal boss component 86 from rotating with respect to the dovetail shaped base component 86, and, in turn, with respect to the respective knee-chassis segment 44, 46. Upon loosening of the set screws 107, it will be apparent to those of ordinary skill that the respective couplings 48, 50 will be rotatably and/or slidably adjustable again.

Therefore, in operation, if the prosthetist wishes to make a rotational and/or translational adjustment of an above-knee or below-knee prosthetic limb component with respect to the knee-chassis component 42 the prosthetist merely needs to loosen the set screws 107 on the pyramid receiver 36 mating with the coupling 48, 50, make the desired rotational and/or translational adjustments, and then merely tighten the set screws 107 again, thereby locking the components from further rotational and/or translational movement. As will be apparent to those of ordinary skill, the exemplary embodiment allows the rotational and/or translational adjustments to be made without requiring the prosthetist to completely de-couple the respective coupling from the above-knee or below-knee prosthetic limb components.

Thus, as will be appreciated by those of ordinary skill in the art, the above exemplary embodiment provides a prosthetic knee-joint assembly that has adjustable pyramid couplings 48, 50 integrated into or with the proximal and distal segments 44, 46 of the knee-chassis 42 to provide rotational and/or lateral adjustability of the knee-joint assembly with respect to above-knee ("AK") and/or below-knee ("BK") prosthetic limb components without significantly increasing the profile (length) of the knee-chassis 42. Such an invention provides the knee-joint assembly with desired rotational and/or lateral adjustability with respect to AK and/or BK prosthetic limb components while better maintaining a proper knee center with respect to knee disarticulations and long AK amputations. As will also be appreciated by those of ordinary skill in the art, the design of the adjustable pyramid couplings 48, 50 utilizing the domed members 78 in conjunction with the convex-shaped lower end 112 of the pyramid receiver 36 provides a certain amount of angular adjustability, which is present in the prior art pyramids 30 and receivers 36 discussed above.

While the couplings 48, 50 of the first exemplary embodiment (as well as the remaining exemplary embodiments described below) are described as adjustable pyramids, it will be appreciated by those ordinary skill that it is within the scope of the invention to utilize other types of adjustable couplings (male, female or otherwise) in place of the adjustable pyramid assemblies. For example, it is within the scope of the invention to integrate adjustable pyramid receivers similar to those described in co-pending U.S. patent application Ser. No. 09/613,977, filed Jul. 11, 2000, into the knee-chassis segments in place of one or both of the adjustable pyramid assemblies in the exemplary embodiment. Likewise, while the mechanical presses described above in the first exemplary embodiment (as well as the remaining exemplary embodiments described below) work in conjunction with the pyramid receivers 36 to lock the couplings from rotational and slidable adjustment, it is within the scope of the invention to utilize alternate mechanical presses and alternate locking mechanisms to lock the adjustable couplings after they have been adjusted as desired. It is also, within the scope of the invention that the releasable lock for locking the rotational adjustment be separate from the releasable lock for locking slidable adjustment. For example, it is within the scope of the invention to utilize mechanical presses or alternate locking mechanisms similar to those described in U.S. Pat. No. 6,033,440 or in co-pending U.S. patent application Ser. No. 09/613,977, filed Jul. 11, 2000. The disclosure of co-pending U.S. patent application Ser. No. 09/613,977, filed Jul. 11, 2000 is incorporated herein by reference.

Additionally, while the couplings 48, 50 of the first exemplary embodiment allow for both rotational and translational adjustments, it is within the scope of the invention to provide couplings that allow fewer degrees of adjustment on either or both of the knee chassis segments 44, 46. For example, the exemplary embodiment illustrated in FIG. 6 allows translational and angular adjustments and the exemplary embodiment illustrated in FIG. 7 allows rotational and angular adjustments.

Figure 6:
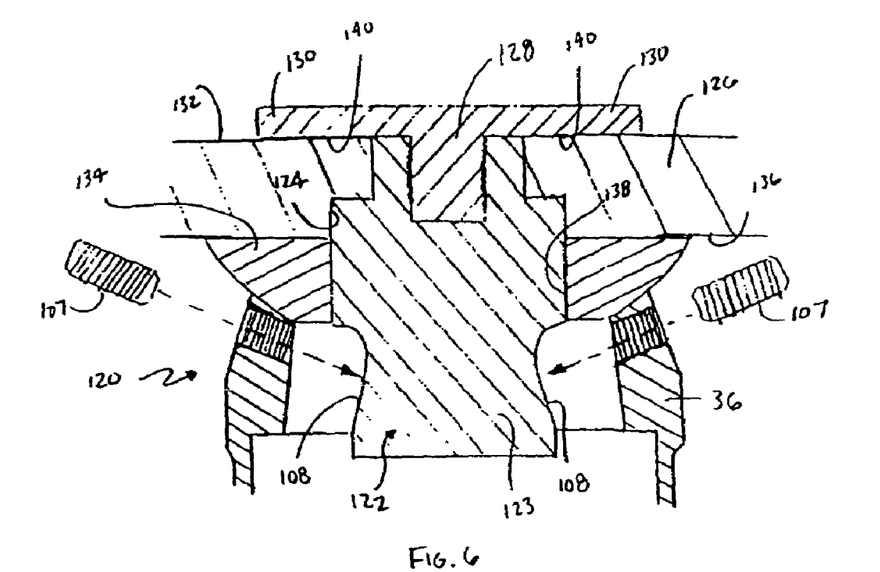
FIG. 6 is a cross-sectional view of a coupling assembly for an alternate embodiment of the present invention.

As shown in FIG. 6, this alternate exemplary embodiment of a coupling 120 that allows translational and angular adjustments includes a pyramidal boss component 122 slidably seated within a stepped groove 124 extending through the respective knee chassis segment's planar base 126 such that the pyramidal boss component 122 is slidable with respect to the planar base 126 in a direction moving into and out of the page as illustrated. The pyramidal boss component 122 is maintained on the planar base 126 by a t-shaped fastener 128 having a pair of wings 130 adapted to extend beyond the stepped groove 124 and slide along the bottom surface 132 of the planar base 126 of the respective knee chassis segment.

The fastener 128 essentially retains, or integrates the coupling 120 with the respective knee chassis segment. An optional dome component 134 may also be provided on an upper surface 136 of the planar base 126 of the knee chassis segment having an axial channel 138 that allows the pyramidal boss component 122 to extend therethrough. To lock the coupling 120, thereby restricting it from translational adjustment, the set screws 107 are tightened against the angled surfaces 108 of the frustopyramidal boss 123 of the pyramidal boss component 122 pushing the pyramidal boss component 122 upwardly such that the upper surfaces 140 of the t-shaped fastener 128 press against the lower planar surface 132 of the base 126 of the respective knee chassis segment, thereby frictionally restricting translational sliding of the coupling 120 with respect to the respective knee chassis segment.

Figure 7:
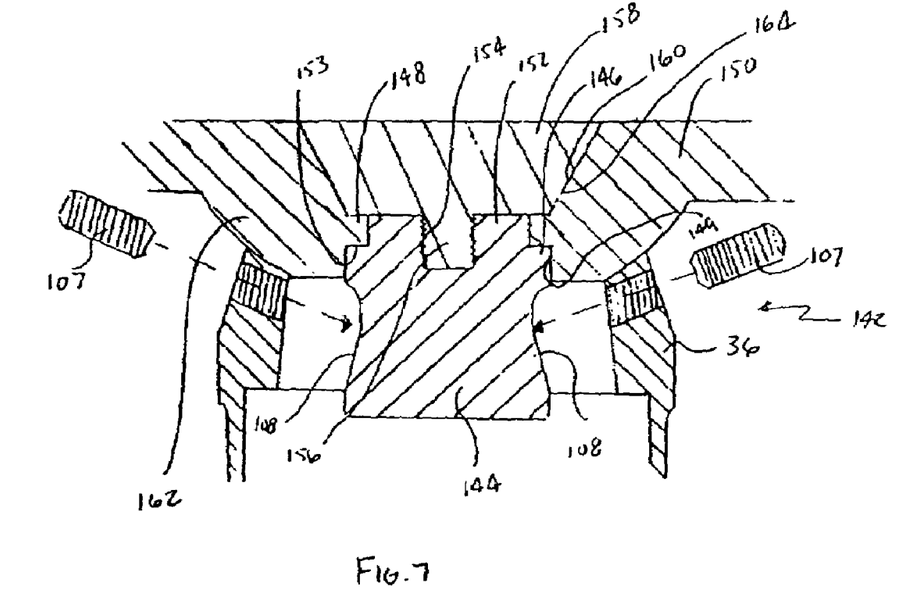
FIG. 7 is a cross-sectional view of a coupling assembly for yet another alternate embodiment of the present invention.

As shown in FIG. 7, this alternate exemplary embodiment of a coupling 142 that allows rotational and angular adjustments includes a pyramidal boss component 144 having an annular flange 146 approximate its lower end seated on an annular shoulder 153 provided by an annular projection 148 extending into an axial channel 149, which extends through the planar base 150. The lower cylindrical portion 152 of the pyramid boss component 144 extends below the annular shoulder 153 and includes a threaded bore 154 extending into the bottom end of the pyramidal boss component 144 that receives a correspondingly threaded axial projection 156 extending upwardly from a frustoconical bearing component 158 that is positioned within a correspondingly-shaped frustoconical portion 160 of the axial channel 149 extending through the planar base 150. An optional dome 162 extends from the upper surface of the planar base 150 (the dome can be a separate component or integrated into the planar base as shown in FIG. 7), where the dome 162 includes the axial channel 149 that allows the pyramidal boss component 144 to extend therethrough. To lock the coupling 142, thereby restricting the pyramid boss and attached frustoconical component 158 from rotational adjustment, the set screws 107 of the pyramid receiver 36 are tightened against the angled surfaces 108 of the frustopyramidal boss component 144 pushing the pyramidal boss component 144 upwardly such that the outer conical surface 164 of the frustoconical fastener component 158 contacts and presses against the complimentary conical surfaces 160 of the frustoconical portion of the channel 149, thereby frictionally restricting rotation of the frustopyramidal boss component 144 with respect to the knee-chassis segment 150.

FIGS. 8 through 11 show an alternative embodiment of the prosthetic knee-joint assembly that provides a knee disarticulation/low-profile version of the knee-joint assembly described above. This embodiment provides a prosthetic knee-joint assembly having an adjustable pyramid coupler integrated into the distal segment of the knee-joint assembly to provide rotational and/or lateral adjustability of the knee-joint assembly with respect to the above-knee ("AK") and/or below-knee ("BK") prosthetic limb components without significantly increasing the profile (length) of the knee-joint assembly. The invention provides the knee-joint assembly with the desired rotational and/or lateral adjustability with respect to BK prosthetic limb components while better maintaining a proper knee center with respect to knee disarticulations and long AK amputations.

Figure 8:
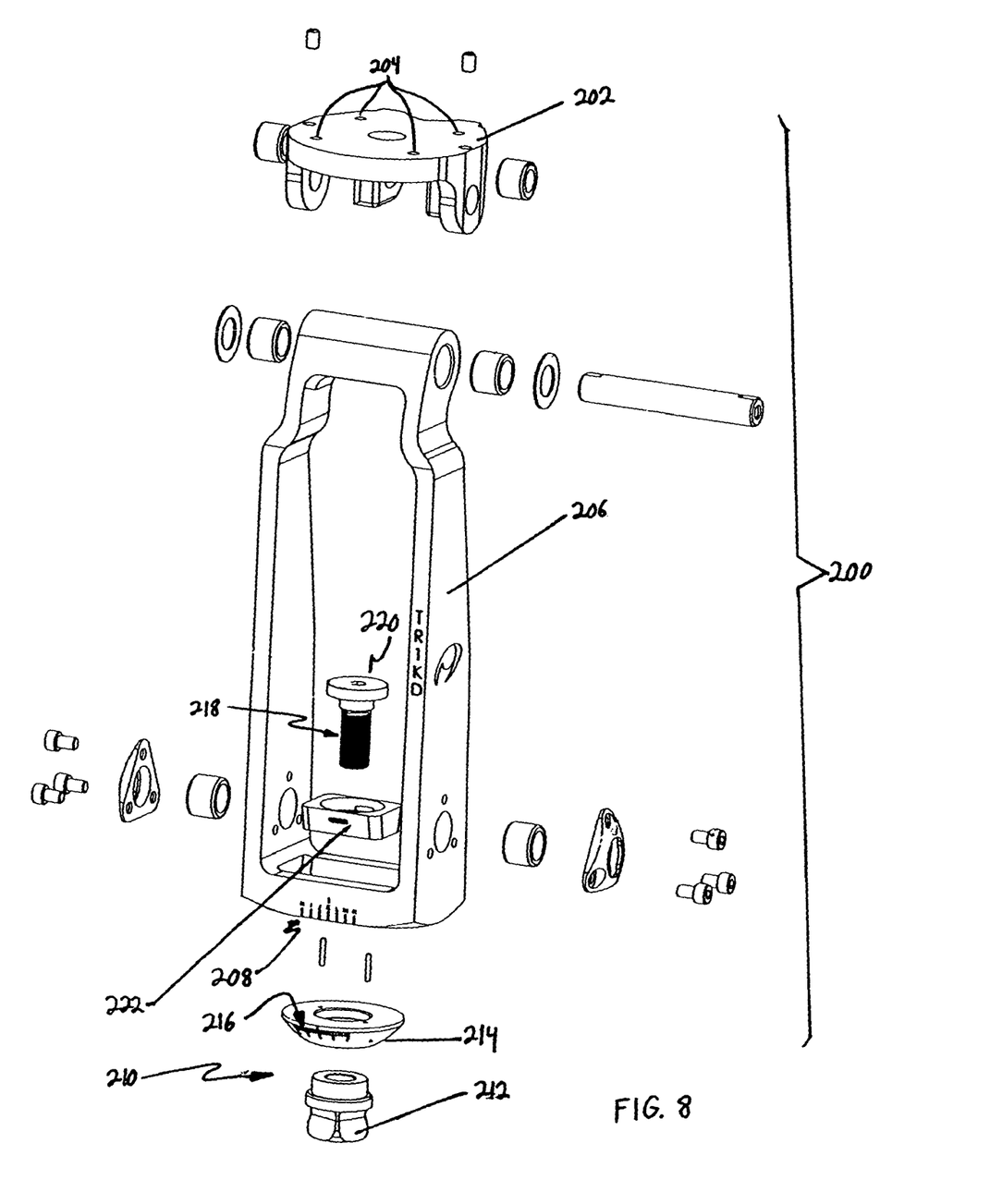
FIGS. 8 through 11 show an alternative embodiment of the prosthetic knee-joint of the present invention.
Figure 9:
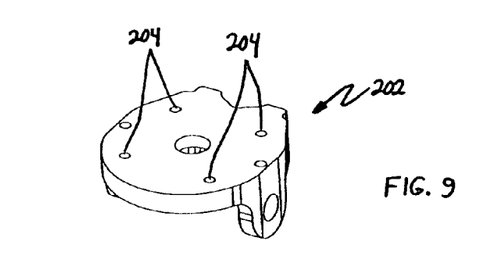
Figure 10:
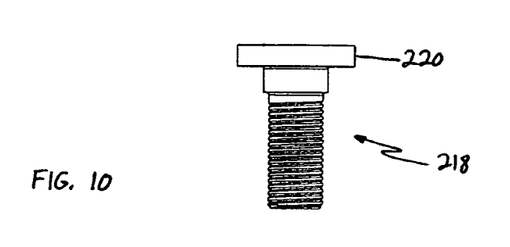

FIG. 8 shows an exploded view of this alternative embodiment of the knee joint. The knee joint chassis 200 shares many general features and attributes with the embodiments described above, and so the differences therefrom will be described here. The top plate or yoke member 202 is specifically designed to be lower in profile than the other embodiments described above, and to provide an optimum bolt connection with the patient's residual limb socket. FIG. 9 shows a closer view of the top plate 202, which includes holes 204 into which bolts can be inserted to join the top plate 202 to a residual limb socket. This design allows the top plate 202 to be bolted directly to the residual limb socket's attachment plate, without the need for a pyramid-type assembly and other prosthetic components between the top plate 202 and the residual limb socket. The top plate 202 depicted in FIGS. 8 and 9 reduces the profile of the knee joint chassis and is adapted to be used in conjunction with a low profile residual limb socket attachment plate, providing further potential reductions in total height. The decreased distance between the top plate 202 of the knee joint chassis 200 and the patient's prosthetic limb socket allows the knee joint to be used with a wider variety of patients, including patients of relatively shorter height and patients with relatively longer residual limbs.

As shown in FIG. 8, the lower, upright component 206 (that is pivotally joined to the top plate/yoke component 202) includes indicia 208 for marking the extent and/or direction of lateral adjustments for the distal pyramid coupling component 210, which includes a pyramidal boss component 212 and a dome component 214. The dome component 214 also includes indicia 216 for indicating the extent and/or direction of rotational adjustments of the pyramid coupler 210 with respect to the indicia 208 on the lower chassis component 206.

Figure 11:
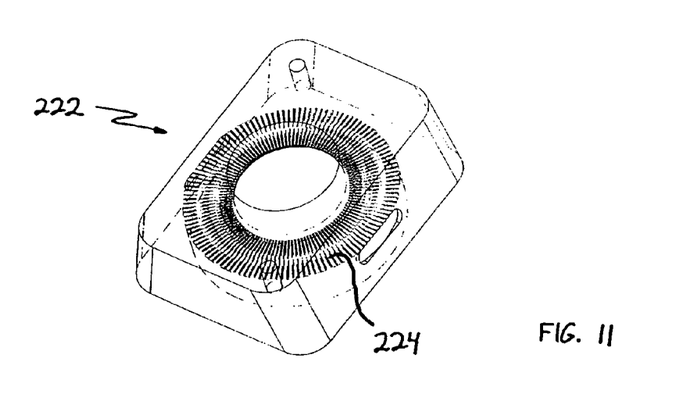

As depicted in FIG. 8, the pyramid coupler 210 is joined to the lower chassis component 206 by a bolt 218, which fits through an opening in a wedge component 222 and secures the pyramidal boss component 212. FIG. 11 shows a close-up, transparent view of the wedge component 222. The inner surface 224 of the wedge component 222, which is adapted to receive the head 220 of the bolt 218, is textured with plurality of radial grooves. This textured surface 224 provides added friction to grip the head 220 of the attachment bolt 218 when rotational adjustments are locked by attachment of a pyramid receiver component to the pyramid coupling 210.

Following from the above detailed description, it will be apparent to those of ordinary skill in the art that, while the apparatuses and processes herein described constitute exemplary embodiments of the present invention, it is understood that the invention is not limited to these precise apparatuses and processes and that changes may be made therein without departing from the scope of the invention as claimed or as illustrated by the various aspects of the present invention set forth in the summary. Additionally, it is to be understood that the invention is defined by the claims and it is not intended that any limitations or elements describing the exemplary embodiments set forth herein are to be incorporated into the meanings of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A prosthetic knee-joint assembly for a prosthetic limb comprising:
    a proximal segment having a surface adapted for mounting to an above-knee prosthetic limb socket;
    a distal segment pivotally disposed with respect to the proximal segment and pivotable with respect to the proximal segment in at least an anterior-posterior direction to provide a knee-joint pivot point; and
    a coupling at least partially integrated within the distal segment, including an adjustable member having a frustopyramidal boss extending distally with respect to the distal segment, the frustopyramidal boss being adapted to mount the distal segment to below-knee prosthetic limb components, and the frustopyramidal boss being slidably adjustable with respect to the distal segment so as to be slidable in at least one of the anterior-posterior and medial-lateral directions, and rotatably adjustable with respect to the distal segment;
    wherein the coupling includes an opening extending through a distal end of the distal segment and a bolt extending through the opening, the bolt including a threaded section;
    wherein the at least a portion of the threaded section releasably engages a corresponding threaded section within the frustopyramidal boss;
    wherein the bolt and the frustopyramidal boss are rotatable relative to the distal segment;
    wherein a position of the fastener within the opening is selectively adjustable in at least one of the anterior-posterior and medial-lateral directions; and
    wherein the coupling selectively inhibits both rotation of the frustopyramidal boss and translation of the frustopyramidal boss in at least one of the anterior-posterior and medial-lateral directions.

2. The prosthetic knee-joint assembly of claim 1, further comprising:
    a first releasable lock adapted to selectively prohibit rotation of the frustopyramidal boss with respect to the distal segment; and
    a second releasable lock adapted to selectively prohibit sliding of the frustopyramidal boss with respect to the distal segment.

3. A prosthetic knee-joint assembly for a prosthetic limb comprising:
    a proximal segment having a surface adapted for mounting to an above-knee prosthetic limb socket;
    a distal segment pivotally disposed with respect to the proximal segment and pivotable with respect to the proximal segment in at least an anterior-posterior direction to provide a knee-joint pivot point;
    a coupling provided with the distal segment, including an adjustable member having a frustopyramidal boss extending distally with respect to the distal segment, the frustopyramidal boss being adapted to mount the distal segment to below-knee prosthetic limb components, and the frustopyramidal boss being slidably adjustable with respect to the distal segment so as to be slidable in at least one of the anterior-posterior and medial-lateral directions, and rotatably adjustable with respect to the distal segment;
    a first releasable lock adapted to selectively prohibit rotation of the frustopyramidal boss with respect to the distal segment; and
    a second releasable lock adapted to selectively prohibit sliding of the frustopyramidal boss with respect to the distal segment; wherein
    the adjustable member is an assembly that includes a sliding member and a rotating member, the sliding member having a cavity occupied by a proximal portion of the rotating member, the cavity having an annular surface that faces, at least partially, the proximal direction; the rotating member including the frustopyramidal boss, which extends distally from the cavity in the sliding member; wherein the proximal portion of the rotating member includes an annular surface complimentary to, substantially coaxial with, and facing the annular surface of the cavity; wherein the sliding member includes a pair of opposed surfaces, each being parallel to the respective direction of slideability, and the pair of opposed surfaces facing at least partially in a distal direction; wherein the distal segment includes a pair of opposed surfaces complimentary to, substantially parallel to, and facing the pair of opposed surfaces of the adjustable member; and wherein the coupling includes a mechanical press operative to pull the frustopyramidal boss in the distal direction, such that the annular surface of the proximal portion of the rotating member engages annular surface of the cavity in the sliding member, thereby providing the first releasable lock, and thereafter upon further application of the mechanical press, the combination of the rotating member and sliding member are pulled in the distal direction such that the pair of opposed surfaces of the sliding member presses against the complimentary pair of opposed surfaces of the distal segment, thereby providing the second releasable lock;

wherein the distal segment includes a distal opening through which the coupling extends.

4. The prosthetic knee-joint assembly of claim 3, wherein the coupling includes a domed member seated on a distal end of the distal segment and having a channel extending axially therethrough; wherein the rotating member extends distally through the axial channel in the domed member such that the frustopyramidal boss extends above an apex of the domed member and such that proximal portion of the rotating member extends beyond a base of the domed member and into the sliding member; wherein the mechanical press is an annular coupling adapter extending from the below-knee prosthetic limb component, the annular coupling adaptor including a central bore receiving the frustopyramidal boss therein, the central bore including an annular mouth abutting against the domed surface of the domed member, and wherein the mechanical press further includes at least two diametrically opposed set screws extending radially into the central bore and angled distally, whereby tightening of the set screws causes the set screws to contact and press against opposed surfaces of the frustopyramidal boss in the central bore such that the rotating member is pushed by the set screws in the distal direction.

5. The prosthetic knee-joint assembly of claim 3, wherein at least one of the annular surface of the proximal portion of the rotating member and the annular surface of the cavity in the sliding member has radial grooves, whereby friction between said two surfaces is increased.

6. The prosthetic knee-joint assembly of claim 3, wherein the frustopyramidal boss is slidable substantially in the medial-lateral direction.

7. The prosthetic knee-joint assembly of claim 3, wherein the sliding member is slidable in the anterior-posterior direction.

8. The prosthetic knee-joint of claim 3, wherein the proximal segment's surface adapted for mounting to an above-knee prosthetic limb socket includes at least one hole adapted to receive a threaded bolt; and wherein the said surface is adapted to be joined to a distal attachment plate of the prosthetic limb socket by one or more bolts.

9. The prosthetic knee-joint of claim 3, wherein at least one of the distal segment and the coupling includes visual indicia for determining the position of the coupling relative to the distal segment.

10. A prosthetic knee-joint assembly for a prosthetic limb comprising:

a proximal segment having a surface adapted for mounting to an above-knee prosthetic limb socket;

a distal segment pivotally disposed with respect to the proximal segment and pivotable with respect to the proximal segment in at least an anterior-posterior direction to provide a knee-joint pivot point; and a male coupling provided on the distal segment, the male coupling including a frustopyramidal boss extending outwardly from the one segment substantially approximate the TKA line, the frustopyramidal boss being adapted to mount the distal segment to a female coupling carried on another prosthetic limb component, and the frustopyramidal boss being slidably adjustable with respect to the distal segment so as to be slidable in at least one direction substantially perpendicular to the TKA line, and the frustopyramidal boss being rotationally adjustable with respect to the distal segment so as to be rotatable with respect to the distal segment on a rotational axis substantially parallel to the TKA line; wherein the male coupling is an assembly that includes a sliding member slidably carried by the distal segment and a rotating member rotatably carried by the sliding member; wherein the rotating member has a first end carried by the sliding member and an opposite end that includes the frustopyramidal boss; wherein the distal segment includes a dove-tall shaped channel at least partially bounding an opening extending trough an end surface thereof; the sliding member includes at least a portion that has a dove-tail shaped cross-section complementary to the dove-tail shaped channel in the distal segment, the portion being slidably carried in the dove-tail shaped channel; and wherein the sliding member includes an annular cavity extending into an end surface thereof, the annular cavity retaining the first end of the rotating member therein; and at least a portion of the male coupling extends through the opening in the distal segment.

11. The prosthetic knee-joint assembly of claim 10, wherein at least one of the surface of the annular cavity and the rotating member has radial grooves, whereby friction between said two surfaces is increased.

12. The prosthetic knee-joint of claim 10, wherein the proximal segment's surface adapted for mounting to an above-knee prosthetic limb socket includes at least one hole adapted to receive a threaded bolt; and wherein the said surface is adapted to be joined to a distal attachment plate of the prosthetic limb socket by one or more bolts.

13. A prosthetic knee-joint assembly for a prosthetic limb comprising:

a proximal segment including a planar proximal surface adapted for mounting to an above-knee prosthetic limb socket;

a distal segment pivotally disposed with respect to the proximal segment, and pivotable with respect to the proximal segment in at least the anterior-posterior direction to provide a knee-joint pivot point, the distal segment including a planar distal surface and a proximal groove extending along an open bottom on a backside of the distal surface;

a coupling including a bearing portion slidably received within the proximal groove and further including a frustopyramidal boss extending in a distal direction from the bearing portion, the frustopyramidal boss being rotatable with respect to the bearing portion and adapted to mount the distal segment to below-knee prosthetic limb components;

a first releasable lock adapted to selectively prohibit rotation of the frustopyramidal boss with respect to the bearing portion; and a second releasable lock adapted to selectively prohibit sliding of the bearing portion in the groove.

14. The prosthetic knee-joint assembly of claim 13, wherein the coupling includes a domed portion positioned distally to the distal surface of the distal segment and to the bearing portion; and wherein the frustopyramidal boss extends from the bearing portion, axially through the domed portion, and out from a distal apex of the domed portion.

15. The prosthetic knee-joint assembly of claim 13, wherein the bearing portion includes a sliding member and a rotating member, the sliding member having a lacuna occupied by a proximal portion of the rotating member, the lacuna having an annular surface that faces, at least partially, the proximal direction; the rotating member including an annular outer surface complimentary to, substantially coaxial to, and facing the annular surface of the lacuna; wherein the frustopyramidal boss is joined to the rotating member and extends distally therefrom; wherein the first releasable lock is operative to press the annular outer surface of the rotating member against the annular surface of the lacuna so as to prohibit rotation of the frustopyramidal boss; wherein the proximal groove includes a pair of longitudinally extending surfaces on opposing lateral sides of the groove, each of the longitudinally extending surfaces facing at least partially proximally; and wherein the bearing portion includes a pair of complimentary surfaces respectively facing the pair of longitudinally extending surfaces of the proximal groove; the second releasable lock is operative to press the pair of complimentary surfaces of the bearing portion against the pair of longitudinally extending surfaces of the proximal groove to prohibit sliding of the bearing portion.

16. The prosthetic knee-joint assembly of claim 15, wherein at least one of the annular outer surface of the rotating member and the annular surface of the lacuna has radial grooves, whereby friction between said two surfaces is increased.

17. The prosthetic knee-joint of claim 13, wherein the proximal segment's surface adapted for mounting to an above-knee prosthetic limb socket includes at least one hole adapted to receive a threaded bolt; and wherein the said surface is adapted to be joined to a distal attachment plate of the prosthetic limb socket by one or more bolts.

18. The prosthetic knee-joint of claim 13, wherein at least one of the distal segment and the coupling includes visual indicia for determining the position of the coupling relative to the distal segment.

19. A prosthetic knee-joint assembly for a prosthetic limb comprising:

a proximal segment having a surface adapted for mounting to an above-knee prosthetic limb socket;

a distal segment pivotally disposed with respect to the proximal segment and pivotable with respect to the proximal segment in at least an anterior-posterior direction to provide a knee-joint pivot point; and a coupling provided with the distal segment, including an adjustable member having a frustopyramidal boss extending distally with respect to the distal segment, the frustopyramidal boss being adapted to mount the distal segment to below-knee prosthetic limb components, and the frustopyramidal boss being slidably adjustable with respect to the distal segment so as to be slidable in at least one of the anterior-posterior and medial-lateral directions, and rotatably adjustable with respect to the distal segment; wherein the distal segment and the coupling include visual indicia for determining the position of the coupling relative to the distal segment.

20. A prosthetic knee-joint assembly for a prosthetic limb comprising:

a proximal segment adapted to be coupled to an above-knee prosthetic limb component;

a distal segment pivotally disposed with respect to the proximal segment and pivotable with respect to the proximal segment in at least an anterior-posterior direction to provide a knee-joint pivot point; and a coupling provided with the distal segment, including an adjustable member having a frustopyramidal boss extending distally with respect to the distal segment, the frustopyramidal boss being adapted to mount the distal segment to below-knee prosthetic limb components, and the frustopyramidal boss being slidably adjustable with respect to the distal segment so as to be slidable in at least one of the anterior-posterior and medial-lateral directions, and rotatably adjustable with respect to the distal segment;

wherein the distal segment includes a through hole limiting medial-lateral travel of the frustopyramidal boss.

* * * * *